(12) United States Patent
Carrier et al.

(10) Patent No.: US 7,543,378 B2
(45) Date of Patent: Jun. 9, 2009

(54) METHOD FOR MANUFACTURING A TEST BAR

(75) Inventors: Charles W. Carrier, West Chester, OH (US); Bernard H. Lawless, West Chester, OH (US)

(73) Assignee: General Electric Company, Schnectady, NY (US)

( * ) Notice: Subject to any disclaimer, the term of this patent is extended or adjusted under 35 U.S.C. 154(b) by 598 days.

(21) Appl. No.: 11/093,595

(22) Filed: Mar. 30, 2005

(65) Prior Publication Data

US 2006/0225277 A1    Oct. 12, 2006

(51) Int. Cl.
*B23P 15/04* (2006.01)
(52) U.S. Cl. .......................... 29/889.2; 73/826
(58) Field of Classification Search ............... 29/889.2; 73/826; 428/137
See application file for complete search history.

(56) References Cited

U.S. PATENT DOCUMENTS 4,606,230 A * 8/1986 Scott et al. .................. 73/856
4,895,750 A * 1/1990 Pratt .......................... 428/137

* cited by examiner

*Primary Examiner*—Rick K Chang
(74) *Attorney, Agent, or Firm*—Bryn T. Lorentz; William Scott Andes

(57) ABSTRACT nethod for manufacturing a test bar from a turbo-machinery component, test bar made in accordance with the method, and turbo-machinery component associated with the method. A component section is obtained from the turbo-machinery component, wherein the component section includes a component portion, and wherein the component portion has a substantially rectangular cross section and has a width. First and second semi-circular cylinders are obtained having a diameter substantially equal to the width of the component portion. The component section is disposed between, and in contact with, the first and second semi-circular cylinders defining a component-section-cylinder assembly having first and second assembly ends. First and second end extensions are obtained. The first end extension is inertia welded to the first assembly end and the second end extension is inertia welded to the second assembly end defining a test-bar stock. The test-bar stock is machined creating the test bar.

14 Claims, 5 Drawing Sheets

METHOD FOR MANUFACTURING A TEST BAR

BACKGROUND OF THE INVENTION

The present invention relates generally to materials testing, and more particularly to a method for manufacturing a test bar, to a test bar, and to apparatus associated therewith.

It is known to machine a test bar from a component, wherein the test bar is machined to include a gage section disposed between two longitudinal end portions. The gage section has a substantially rectangular cross section. Each longitudinal end portion terminates in a circular end face having a diameter larger than the width of the gage section. In one example, the longitudinal end portions of the test bar are secured to a materials testing device which places the test bar in tension to determine the strength of the gage section. In one application, test results are used to choose materials for the component, to choose dimensions for the component, etc.

Some components, such as some gas-turbine-engine casings, are too thin to have test bars machined therefrom because there is not enough material in the casing to machine the relatively large, circular, longitudinal end portions of a test bar needed to fit conventional testing devices. It is known to obtain a casing section from the casing wherein the casing section has a substantially rectangular cross section and serves as the gage section of a test bar. It is further known to weld, including inertia weld, end extensions to the casing section to create a test bar, wherein the end extensions have large, circular longitudinal end portions which fit conventional testing devices. However, because of the weldability of many alloys, this method has limited success in obtaining accurate test data.

Still, scientists and engineers continue to seek improved methods for manufacturing test bars.

BRIEF DESCRIPTION OF THE INVENTION

A first method of the invention is for manufacturing a test bar from a gas-turbine-engine casing and includes steps a) through f). Step a) includes obtaining a casing section from the gas-turbine-engine casing, wherein the casing section includes a casing portion, and wherein the casing portion has a substantially rectangular cross section and has a width. Step b) includes obtaining first and second semi-circular cylinders having a diameter substantially equal to the width of the casing portion. Step c) includes positioning the casing section between, and in contact with, the first and second semi-circular cylinders defining a casing-section-cylinder assembly having first and second assembly ends. Step d) includes obtaining first and second end extensions. Step e) includes inertia welding the first end extension to the first assembly end and the second end extension to the second assembly end defining a test-bar stock. Step f) includes machining the test-bar stock creating the test bar. The test bar has a gage section from the casing portion of the test-bar stock, wherein the gage section has a cross section substantially identical to the substantially rectangular cross section of the casing portion of the test-bar stock. The test bar has ends having a diameter greater than the width of the casing portion of the test-bar stock.

A second method of the invention is for manufacturing a test bar from a gas-turbine-engine compressor or turbine spool having a longitudinal axis and including two stages connected by a spacer arm having two arm segments joined at a weld. The second method includes steps a) through f). Step a) includes obtaining a spool section from the gas-turbine-engine compressor or turbine spool, wherein the spool section longitudinally includes the spacer arm, and wherein the spacer arm of the spool section has a substantially rectangular cross section and has a width. Step b) includes obtaining substantially-identical, first and second semi-circular cylinders having a diameter substantially equal to the width of the spacer arm of the spool section. Step c) includes positioning the spool section between, and in contact with, the first and second semi-circular cylinders defining a spool-cylinder assembly having first and second assembly ends. Step d) includes obtaining first and second end extensions. Step e) includes inertia welding the first end extension to the first assembly end and the second end extension to the second assembly end defining a test-bar stock. Step f) includes machining the test-bar stock creating the test bar. The test bar has a gage section from the spacer arm of the test-bar stock, wherein the gage section has a cross section substantially identical to the substantially rectangular cross section of the spacer arm of the test-bar stock. The test bar has ends having a diameter greater than the width of the spacer arm of the test-bar stock.

A third method of the invention is for manufacturing a test bar from a turbo-machinery component and includes steps a) through f). Step a) includes obtaining a component section from the turbo-machinery component, wherein the component section includes a component portion, and wherein the component portion has a substantially rectangular cross section and has a width. Step b) includes obtaining first and second semi-circular cylinders having a diameter substantially equal to the width of the component portion. Step c) includes positioning the component section between, and in contact with, the first and second semi-circular cylinders defining a component-section-cylinder assembly having first and second assembly ends. Step d) includes obtaining first and second end extensions. Step e) includes inertia welding the first end extension to the first assembly end and the second end extension to the second assembly end defining a test-bar stock. Step f) includes machining the test-bar stock creating the test bar. The test bar has a gage section from the component portion of the test-bar stock, wherein the gage section has a cross section substantially identical to the substantially rectangular cross section of the component portion of the test-bar stock. The test bar has ends having a diameter greater than the width of the component portion of the test-bar stock.

Applicants have performed experiments which obtained accurate test data from test bars manufactured from gas-turbine-engine casings in accordance with the steps of the above-described methods.

BRIEF DESCRIPTION OF THE DRAWING

The accompanying drawing illustrates an embodiment of the invention wherein.

DETAILED DESCRIPTION OF THE INVENTION

Figure 1:
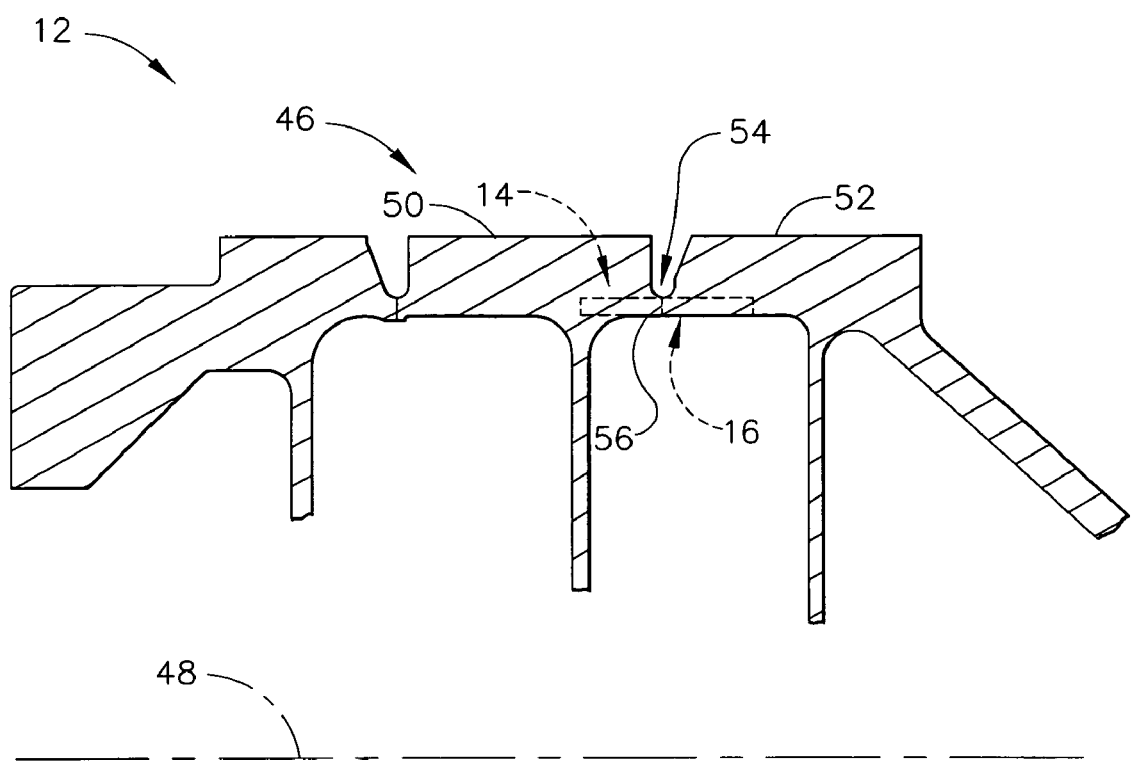
FIG. 1 is an above-axis, side-elevational, cut-away, schematic view of a portion of a gas-turbine-engine casing (which is in the form of a gas-turbine-engine compressor spool and which is an example of a turbo-machinery component) including a dash-line portion representing a casing section that is obtained therefrom in step a) of one method for manufacturing a test bar.

Referring now to FIGS. 1-4 of the drawings, a first method of the invention is for manufacturing a test bar from a gas-turbine-engine casing 12 and includes steps a) through f). Step a) includes obtaining a casing section 14 (see FIGS. 1 and 2) from the gas-turbine-engine casing 12, wherein the casing section 14 includes a casing portion 16, and wherein the casing portion 16 has a substantially rectangular cross section and has a width 18. Step b) includes obtaining first and second semi-circular cylinders 20 and 22 having a diameter substantially equal to the width 18 of the casing portion 16. Step c) includes positioning the casing section 14 between, and in contact with, the first and second semi-circular cylinders 20 and 22 (see FIG. 3) defining a casing-section-cylinder assembly 24 having first and second assembly ends 26 and 28. Step d) includes obtaining first and second end extensions 30 and 32. Step e) includes inertia welding the first end extension 30 to the first assembly end 26 and the second end extension 32 to the second assembly end 28 defining a test-bar stock 34 (see FIG. 4). Step f) includes machining the test-bar stock 34 creating the test bar 36 (see the dash line portion of FIG. 4). The test bar 36 has a gage section 38 from the casing portion 16 of the test-bar stock 34, wherein the gage section 38 has a cross section substantially identical to the substantially rectangular cross section of the casing portion 16 of the test-bar stock 34. The test bar 36 has ends 40 and 42 having a diameter greater than the width of the casing portion 16 of the test-bar stock 34.

Examples of gas-turbine-engine casings include, without limitation, fan casings, compressor casings, combustor casings, and turbine casings. Techniques for obtaining a casing section include, without limitation, cutting, machining, etc the casing.

Figure 2:
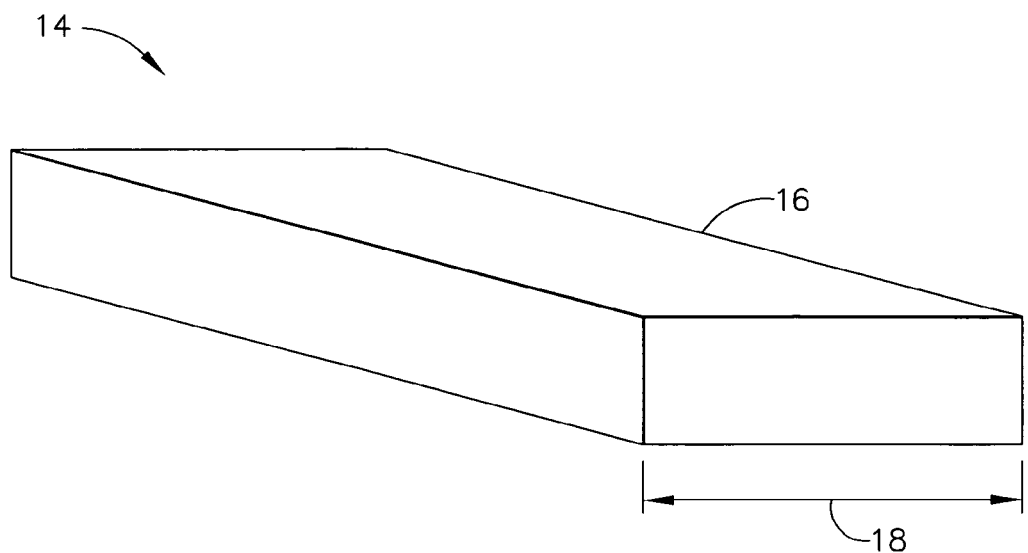
FIG. 2 is a perspective view of the casing section obtained from the gas-turbine-engine compressor spool of FIG. 1.
Figure 3:
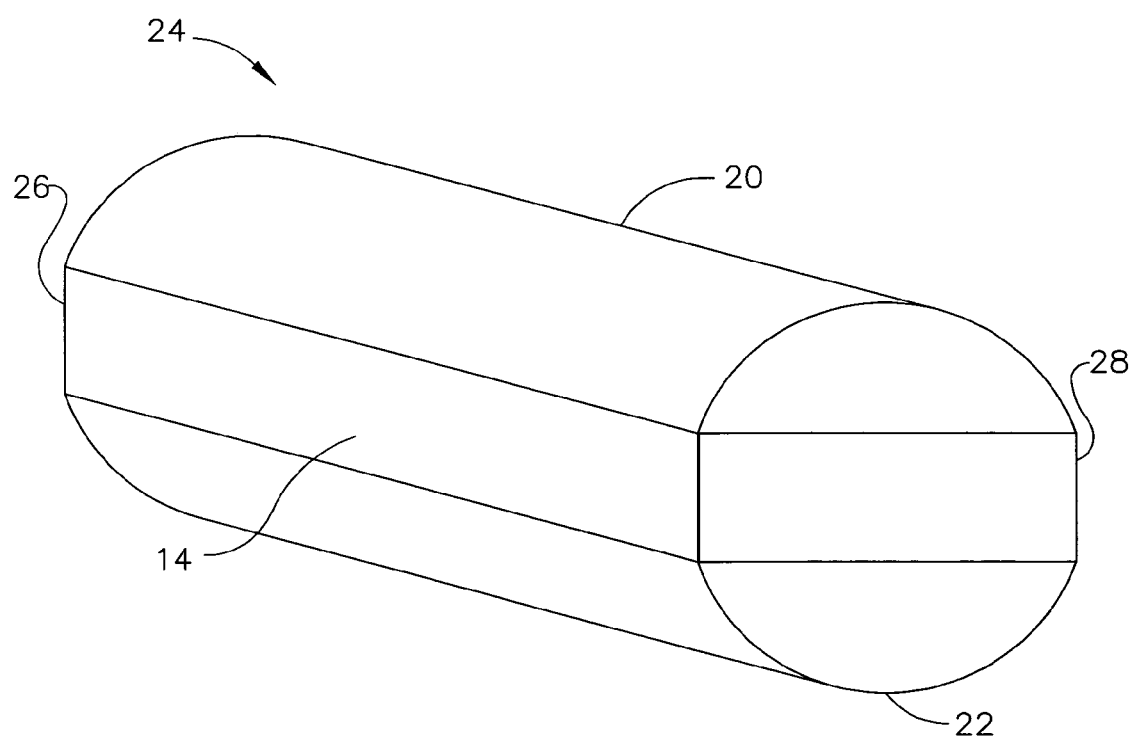
FIG. 3 is a perspective view of the casing section of FIG. 2 positioned between first and second semi-circular cylinders creating a casing-section-cylinder assembly in accordance with step c) of the one method.
Figure 4:
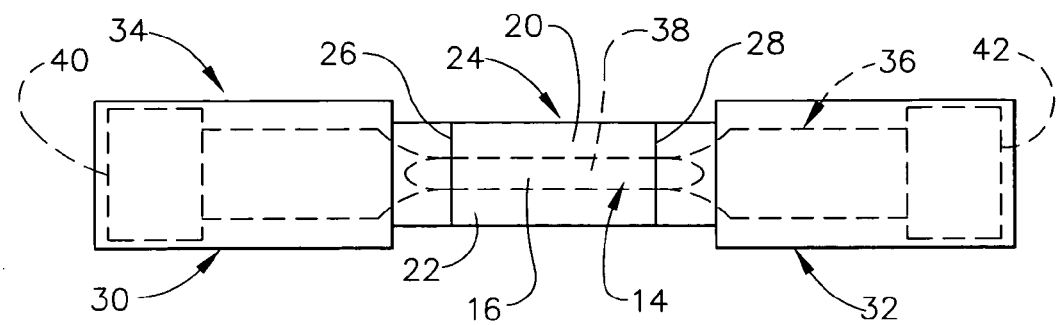
FIG. 4 is a side elevational view of the assembly of FIG. 3 with first and second end extensions inertia welded thereto defining a test-bar stock in accordance with step e) of the one method, wherein the dashed-line portion represents the test bar created from machining the test-bar stock in accordance with step f) of the one method.
Figure 5:
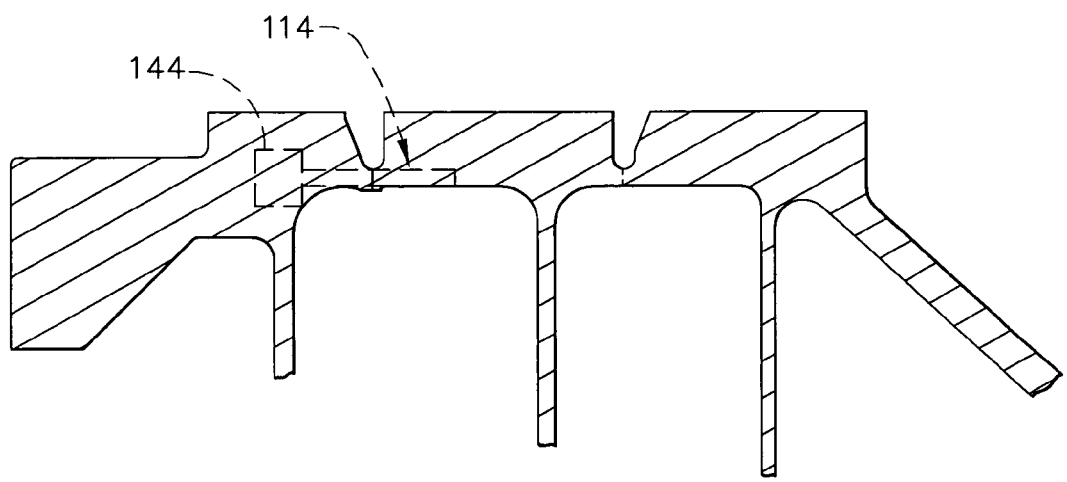
FIG. 5 is a view, as in FIG. 1, but with a different dash-line portion representing a different casing section for manufacturing a different test bar.

In a first illustration of the first method, the entire casing section 14 has a substantially rectangular cross section, as can be appreciated from FIG. 2, wherein there is not enough material in the casing to obtain a casing section which can include any other portion of the test bar. In one variation, the first and second semi-circular cylinders 20 and 22 are substantially identical, and the first and second end extensions 30 and 32 are substantially identical. In one modification, the first end extension 30 includes a longitudinally inward portion having a diameter substantially equal to the width 18 of the casing portion 16 of the test-bar stock 34, and the first end extension 30 includes a longitudinally outward portion having a diameter greater than the diameter of the longitudinally inward portion.

In the same or a different variation of the first illustration, the width of the casing portion 16 of the test-bar stock 34 is not larger than the diameters of the first and second semi-circular cylinders 20 and 22. In one example, this assures that the clamping load applied to the casing portion 16 is evenly distributed in step e). In one modification, the length of the casing section 14 is substantially equal to, but not larger than, the length of the first and second semi-circular cylinders 20 and 22. In one example, this allows the initial weld load in step e) to be applied to the first and second semi-circular cylinders 20 and 22, wherein this action forces these pieces fully into the inertia-welding tooling (not shown) at the beginning of the weld cycle thereby eliminating any mismatch in lengths on the opposite end, and wherein, when the casing-section-cylinder assembly is then reversed for the second weld, all mismatches in length have been eliminated. In one employment, the first and second semi-circular cylinders 20 and 22 are up to 0.25 millimeters longer than the casing section 14.

In one construction of the first illustration, the gas-turbine-engine casing 12 has an inner diameter of substantially 55.88 centimeters and has a thickness from 0.23 centimeters to over 2.54 centimeters (and in one example a thickness of substantially 2.03 inches, the casing portion 16 has a width 18 of substantially 1.59 centimeters, the longitudinal ends of the test bar 36 have a diameter of substantially 1.91 centimeters, and the casing section 14 has a length of substantially 5.08 centimeters or less.

Figure 6:
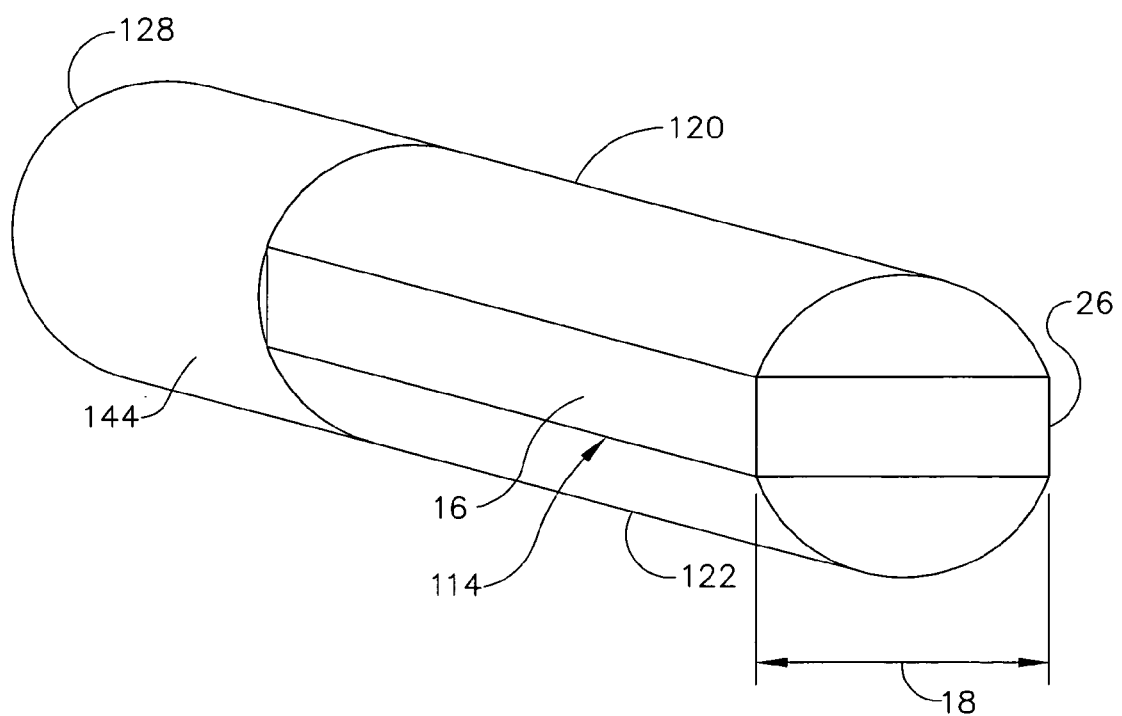
FIG. 6 is a view, as in FIG. 3, but with the different casing section of FIG. 5.

In a second illustration of the first method, and referring to FIGS. 5-8 showing a different embodiment of a casing section 114, the casing section 114 includes a single substantially-right-circular cylindrical end portion 144 having a diameter substantially equal to the diameter of a longitudinally inward portion of the second end extension 132. The second assembly end 128 is the substantially-right-circular cylindrical end portion 144. Step c) disposes the first and second semi-circular cylinders 120 and 122 longitudinally against a longitudinally inward side of the substantially-right-circular cylindrical end portion 144 of the casing section 114, as shown in FIG. 6. In one variation, the first end extension 30 includes a longitudinally inward portion having a diameter substantially equal to the width 18 of the casing portion 16 of the test-bar stock, and the first end extension 30 includes a longitudinally outward portion having a diameter greater than the diameter of the longitudinally inward portion of the first end extension 30.

In the same or a different variation of the second illustration, the width 18 of the casing portion 16 of the test-bar stock is not larger than the diameters of the first and second semi-circular cylinders 120 and 122. In one modification, the length of the casing section 114, other than the substantially-right-circular cylindrical end portion 144, is substantially equal to, but not larger than, the length of the first and second semi-circular cylinders 120 and 122.

Figure 7:
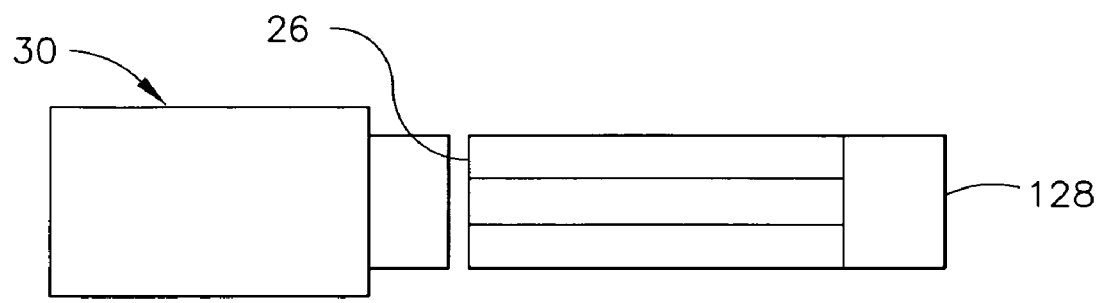
FIG. 7 is side elevational view of the assembly of FIG. 6 positioned to first inertia weld the first end extension to the first assembly end.
Figure 8:
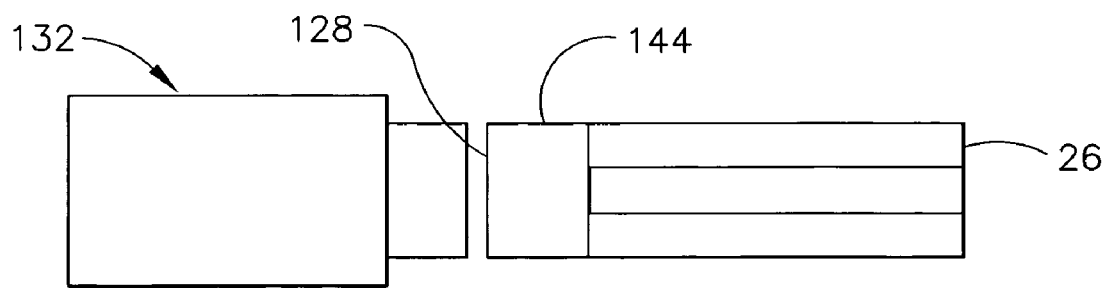
FIG. 8 is side elevational view of the assembly of FIG. 6 positioned to first inertia weld the second end extension to the second assembly end.

In one enablement of the second illustration, as shown in FIG. 7, step e) inertia welds the first end extension 30 to the first assembly end 26 before inertia welding the second end extension 132 to the second assembly end 128. In a different enablement, as shown in FIG. 8, step e) inertia welds the second end extension 132 to the second assembly end 128 before inertia welding the first end extension 30 to the first assembly end 26.

A first expression of an embodiment of FIGS. 1-4 is for apparatus comprising a gas-turbine-engine casing 12 having at least one of a material composition and a dimension chosen at least in part from testing a test bar 36 made in accordance with the steps of the first method. A second expression of an embodiment of FIGS. 1-4 is for a test bar 36 made in accordance with the steps of the first method.

A second method of the invention is for manufacturing a test bar from a gas-turbine-engine compressor or turbine spool 46 having a longitudinal axis 48 and including two stages 50 and 52 connected by a spacer arm 54 having two arm segments joined at a weld. The second method comprises steps a) through f). It is noted that a gas-turbine-engine compressor or turbine spool 46 is an example of a gas-turbine engine casing 12 previously discussed in the first method. Step a) includes obtaining a spool section from the gas-turbine-engine compressor or turbine spool, wherein the spool section longitudinally includes the spacer arm, and wherein the spacer arm of the spool section has a substantially rectangular cross section and has a width. Step b) includes obtaining substantially-identical, first and second semi-circular cylinders having a diameter substantially equal to the width of the spacer arm of the spool section. Step c) includes disposing the spool section between, and in contact with, the first and second semi-circular cylinders defining a spool-cylinder assembly having first and second assembly ends. Step d) includes obtaining first and second end extensions. Step e) includes inertia welding the first end extension to the first assembly end and the second end extension to the second assembly end defining a test-bar stock. Step f) includes machining the test-bar stock creating the test bar. The test bar has a gage section from the spacer arm of the test-bar stock, wherein the gage section has a cross section substantially identical to the substantially rectangular cross section of the spacer arm of the test-bar stock. The test bar has ends having a diameter greater than the width of the spacer arm of the test-bar stock.

A third expression of an embodiment of FIGS. 1-4 is for apparatus comprising a compressor or turbine spool 46 having at least one of a material composition and a dimension chosen at least in part from testing a test bar 36 made in accordance with the steps of the second method. A fourth expression of an embodiment of FIGS. 1-4 is for a test bar 36 made in accordance with the steps of the second method.

A third method of the invention is for manufacturing a test bar from a turbo-machinery component (an example of which is the gas-turbine-engine casing 12 previously discussed in the first method). The third method includes steps a) through f). Step a) includes obtaining a component section from the turbo-machinery component, wherein the component section includes a component portion, and wherein the component portion has a substantially rectangular cross section and has a width. Step b) includes obtaining first and second semi-circular cylinders having a diameter substantially equal to the width of the component portion. Step c) includes disposing the component section between, and in contact with, the first and second semi-circular cylinders defining a component-section-cylinder assembly having first and second assembly ends. Step d) includes obtaining first and second end extensions. Step e) includes inertia welding the first end extension to the first assembly end and the second end extension to the second assembly end defining a test-bar stock. Step f) includes machining the test-bar stock creating the test bar. The test bar has a gage section from the component portion of the test-bar stock, wherein the gage section has a cross section substantially identical to the substantially rectangular cross section of the component portion of the test-bar stock. The test bar has ends having a diameter greater than the width of the component portion of the test-bar stock.

A fifth expression of an embodiment of FIGS. 1-4 is for apparatus comprising a turbo-machinery component having at least one of a material composition and a dimension chosen at least in part from testing a test bar made in accordance with the steps of the third method. A sixth expression of an embodiment of FIGS. 1-4 is for a test bar made in accordance with the steps of the third method.

While the present invention has been illustrated by a description of several methods and expressions of embodiments, it is not the intention of the applicants to restrict or limit the spirit and scope of the appended claims to such detail. Numerous other variations, changes, and substitutions will occur to those skilled in the art without departing from the scope of the invention.

The invention claimed is:

1. A method for manufacturing a test bar from a gas-turbine-engine casing, wherein the method comprises the steps of:
   a) obtaining a casing section from the gas-turbine-engine-casing, wherein the casing section includes a casing portion, and wherein the casing portion has a substantially rectangular cross section and has a width;
   b) obtaining first and second semi-circular cylinders having a diameter substantially equal to the width of the casing portion;
   c) disposing the casing section between, and in contact with, the first and second semi-circular cylinders defining a casing-section-cylinder assembly having first and second assembly ends;
   d) obtaining first and second extensions;
   e) inertia welding the first end extension to the first assembly end and the second end extension to the second assembly end defining a test-bar stock; and
   f) machining the test-bar stock creating the test bar, wherein the test bar has a gage section from the casing portion of the test-bar stock, wherein the gage section has a cross section substantially identical to the substantially rectangular cross section of the casing portion of the test-bar stock, and wherein the test bar has ends having a diameter greater than the width of the casing portion of the test-bar stock.

2. The method of claim 1, wherein an entire casing section has a substantially rectangular cross section.

3. The method of claim 2, wherein the first and second semi-circular cylinders are substantially identical, and wherein the first and second end extensions are substantially identical.

4. The method of claim 3, wherein the first end extension includes a longitudinally inward portion having a diameter substantially equal to the width of the casing portion of the test-bar stock, and wherein the first end extension includes a longitudinally outward portion having a diameter greater than the diameter of the longitudinally inward portion.

5. The method of claim 2, wherein the width of the casing portion of the test-bar stock is not larger than the diameters of the first and second semi-circular cylinders.

6. The method of claim 5, wherein the length of the casing section is substantially equal to, but not larger than, the length of the first and second semi-circular cylinders.

7. The method of claim 1, wherein the casing section includes a single substantially-right-circular cylindrical end portion having a diameter substantially equal to the diameter of a longitudinally inward portion of the second end extension, wherein the second assembly end is the substantially-right-circular cylindrical end portion, and wherein step c) disposes the first and second semi-circular cylinders longitudinally against a longitudinally inward side of the substantially-right-circular cylindrical end portion of the casing section.

8. The method of claim 7, wherein the first end extension includes a longitudinally inward portion having a diameter substantially equal to the width of the casing portion of the test-bar stock, and wherein the first end extension includes a longitudinally outward portion having a diameter greater than the diameter of the longitudinally inward portion of the first end extension.

9. The method of claim 7, wherein the width of the casing portion of the test-bar stock is not larger than the diameters of the first and second semi-circular cylinders.

10. The method of claim 9, wherein the length of the casing section, other than the substantially-right-circular cylindrical end portion, is substantially equal to, but not larger than, the length of the first and second semi-circular cylinders.

11. The method of claim 10, wherein step e) inertia welds the first end extension to the first assembly end before inertia welding the second end extension to the second assembly end.

12. The method of claim 10, wherein step e) inertia welds the second end extension to the second assembly end before inertia welding the first end extension to the first assembly end.

13. A method for manufacturing a test bar from a gas-turbine-engine compressor or turbine spool having a longitudinal axis and including two stages connected by a spacer arm having two arm segments joined at a weld, and wherein the method comprises the steps of:
 a) obtaining a spool section from the gas-turbine-engine compressor or turbine spool, wherein the spool section longitudinally includes the spacer arm, and wherein the spacer arm of the spool section has a substantially rectangular cross section and has a width;
 b) obtaining substantially-identical, first and second semi-circular cylinders having a diameter substantially equal to the width of the spacer arm of the spool section;
 c) disposing the spool section between, and in contact with, the first and second semi-circular cylinders defining a spool-cylinder assembly having first and second assembly ends;
 d) obtaining first and second end extensions;
 e) inertia welding the first end extension to the first assembly end and the second end extension to the second assembly end defining a test-bar stock; and
 f) machining the test-bar stock creating the test bar, wherein the test bar has a gage section from the spacer arm of the test-bar stock, wherein the gage section has a cross section substantially identical to the substantially rectangular cross section of the spacer arm of the test-bar stock, and wherein the test bar has ends having a diameter greater than the width of the spacer arm of the test-bar stock.

14. A method for manufacturing a test bar from a turbo-machinery component, wherein the method comprises the steps of:
 a) obtaining a component section from the turbo-machinery component, wherein the component section includes a component portion, and wherein the component portion has a substantially rectangular cross section and has a width;
 b) obtaining first and second semi-circular cylinders having a diameter substantially equal to the width of the component portion;
 c) disposing the component section between, and in contact with, the first and second semi-circular cylinders defining a component-section-cylinder assembly having a first and second assembly ends;
 d) obtaining first and second end extensions;
 e) inertia welding the first end extension to the first assembly end and the second end extension to the second assembly end defining a test-bar stock; and
 f) machining the test-bar stock creating the test bar, wherein the test bar has a gage section from the component portion of the test-bar stock, wherein the gage section has a cross section substantially identical to the substantially rectangular cross section of the component portion of the test-bar stock, and wherein the test bar has ends having a diameter greater than the width of the component portion of the test-bar stock.

\* \* \* \* \*